(12) United States Patent  
Darcey (10) Patent No.: US 6,712,780 B2
(45) Date of Patent: Mar. 30, 2004

(54) CUSTOM-FORMABLE KNEE IMMOBILIZER PRODUCT, KNEE IMMOBILIZER AND METHOD

(75) Inventor: Thomas D. Darcey, Mooresville, NC (US)

(73) Assignee: BSN Medical Inc., Wilmington, DE (US)

( * ) Notice: Subject to any disclaimer, the term of this patent is extended or adjusted under 35 U.S.C. 154(b) by 0 days.

(21) Appl. No.: 10/271,961

(22) Filed: Oct. 15, 2002

(65) Prior Publication Data

US 2003/0045820 A1 Mar. 6, 2003

Related U.S. Application Data

(63) Continuation of application No. 09/731,485, filed on Dec. 7, 2000, now Pat. No. 6,464,658.

(51) Int. Cl.⁷ .................................................. A61F 5/00
(52) U.S. Cl. .............................. 602/8; 5/6; 5/23; 5/26
(58) Field of Search .............................. 602/5, 6, 8, 23, 602/26

(56) References Cited

U.S. PATENT DOCUMENTS

| | | |
|---|---|---|
| 2,103,942 A | 12/1937 | Gillin |
| 3,703,171 A * | 11/1972 | Schiavitto |
| 3,955,565 A | 5/1976 | Johnson, Jr. |
| 4,013,070 A * | 3/1977 | Harroff |
| 4,425,912 A | 1/1984 | Harper |
| 4,427,002 A | 1/1984 | Baron et al. |
| 4,433,680 A | 2/1984 | Yoon |
| 4,442,833 A | 4/1984 | Dahlen et al. |
| 4,502,479 A | 3/1985 | Garwood et al. |
| 4,570,622 A | 2/1986 | von Bonin et al. |
| 4,572,171 A | 2/1986 | Wagner et al. |
| 4,628,917 A | 12/1986 | Campagna, Jr. et al. |
| 4,770,299 A | 9/1988 | Parker |
| D307,054 S | 4/1990 | Johnson, Jr. |
| 5,027,803 A | 7/1991 | Scholz et al. |
| 5,088,478 A | 2/1992 | Grim |
| 5,230,335 A | 7/1993 | Johnson, Jr. et al. |
| 5,248,292 A * | 9/1993 | Holland |
| 5,393,303 A | 2/1995 | Shiono |
| 5,454,780 A | 10/1995 | Duback et al. |
| 5,637,077 A * | 6/1997 | Parker |
| 5,993,405 A * | 11/1999 | Wynn |
| 6,134,720 A * | 10/2000 | Foreman |
| 6,283,810 B1 | 9/2001 | Evans |
| 6,464,658 B1 | 10/2002 | Darcey |

* cited by examiner

Primary Examiner—Nicholas D. Lucchesi
Assistant Examiner—Lalita M. Hamilton
(74) Attorney, Agent, or Firm—Adams Evans P.A.

(57) ABSTRACT

A knee immobilizer for being custom-formed to the shape of a knee while flexible and upon hardening providing a rigid, knee-supporting custom fit. The knee immobilizer includes an elongate splint with a substrate impregnated or coated with a reactive system. The system hardens upon exposure to moisture to form a rigid, self-supporting structure. A flexible cover overlies the substrate for forming an integrated splint structure for being molded while flexible to an aspect of the knee. A bandage extends around the knee for holding the splint in a supporting position on the knee. A splint support cooperates with the splint and the bandage for maintaining the splint on the bandage in a conforming shape against the knee and substantially immobilizing the knee in a predetermined position.

5 Claims, 13 Drawing Sheets

CUSTOM-FORMABLE KNEE IMMOBILIZER PRODUCT, KNEE IMMOBILIZER AND METHOD

TECHNICAL FIELD AND BACKGROUND OF THE INVENTION

This invention relates to a custom-formable knee immobilizer product, knee immobilizer and method.

The invention has particular application in the orthopedic medical field, where injured or diseased knees are often supported and immobilized with a splint or brace so that the patient can continue to walk, albeit with a stiff leg, while the injury heals. Typical injuries which can sometimes require immobilization may include, but are not limited to, pulled or torn quadriceps muscles and tendons and/or the patellar tendon, chondromalacia patellae, pulled or torn medial or lateral collateral ligaments, and posterior or anterior cruciate ligaments. Certain related degenerative conditions, as well post-operative recovery and therapy following a wide range of orthopedic surgical procedures, may also require immobilization of the knee.

In such cases, it is essential to immobilize the knee in such a way as to prevent articulation, which can strain healing muscles, tendons, ligaments and bone surfaces. In addition, the knee must be stabilized to prevent eversion and inversion.

The invention of the present application takes advantage of polymer chemistry to permit quick and easy molding of an immobilizer to the knee and adjacent thigh and calf portions of the leg. The close, custom fit achieved is in distinct contrast to so-called "one size fits all" braces or splints wherein bendable plastic rods or stays provide support, and are held in place by a heavy fabric tube.

The particular embodiment of the immobilizer disclosed in this application will accommodate a wide range of sizes and can be fitted to either the right or left knee. Thus, a much reduced inventory is required. This feature also substantially reduces design and manufacturing costs, and promotes use through ease of fitting. The custom-fit of the immobilizer not only permits easy removal for bathing, dressing or adjustment, but also easy and mistake-proof replacement even by children.

Prior art immobilizers include numerous types of splints and braces which typically include a soft component to place near the skin and a semi-rigid metal or plastic stays which are bent into a shape conforming to the aspect of the knee against which the stay resides. The soft component, for example, fiber padding, foam or an air bladder, is intended not only to provide a cushion, but also to accommodate itself to the varying configurations of differing sized and shaped body parts. For this reason, the cushioned part is substantially greater in thickness than required merely to provide the protection from injury or irritation caused by direct contact with the stays.

Some prior art knee braces include stays which are constructed of thermosetting materials which are heated and then formed to the body while heated. These products require a source of heat, and are susceptible to either over-or-underheating. In addition, body heat itself can soften or increase the flexibility of the stays, thereby decreasing the effectiveness of the protection offered.

The present invention permits quick and easy application of a immobilizer to a knee in such a way as to achieve a true custom fit. The moisture curable resin system used results in a very rigid splint which holds the shape of the molded splint to a very high degree. No heat is required, and a source of water is the only additional material necessary to achieve a cure. Atmospheric moisture alone will cure the splint into its hardened position in a relatively short period of time, but in practice the resin in or on the splint will typically be activated by dipping the splint in water and then removing the excess water by rolling the splint in a towel immediately before the splint is applied to the knee.

SUMMARY OF THE INVENTION

Therefore, it is an object of the invention to provide a custom-formable knee immobilizer.

It is another object of the invention to provide a knee immobilizer which can be molded to a knee to stabilize the knee against articulation, eversion and inversion.

It is another object of the invention to provide a knee immobilizer which can be custom-formed to a particular patient.

It is another object of the invention to provide knee immobilizer having a shape which permits it to be used on either the left or the right knee.

It is another object of the invention to provide knee immobilizer which hardens in the presence of moisture to form a very rigid but very lightweight splint portion.

It is another object of the invention to provide a knee immobilizer which is stored in a moisture-proof pouch until ready for being custom-fitted to the knee.

It is another object of the invention to provide a knee immobilizer which is custom-molded to a patient's knee in such a way that it can be initially held in place with an elongate elastic strip to reduce edema, and thereafter held in place with a strap or straps during later stages of healing.

These and other objects of the present invention are achieved in the preferred embodiments disclosed below by providing a knee immobilizer for being custom-formed to the shape of a knee while flexible and upon hardening providing a rigid, knee-supporting custom fit. The knee immobilizer includes an elongate splint with a substrate impregnated or coated with a reactive system. The system hardens upon exposure to moisture to form a rigid, self-supporting structure. A flexible outer cover overlies the substrate for forming an integrated splint structure for being molded while flexible to an aspect of the knee. The immobilizer also includes a bandage for extending around the knee and holding the splint in a supporting position on the knee. A splint support cooperates with the splint and the bandage for maintaining the splint on the bandage in a conforming shape against the knee and substantially immobilizing the knee in a predetermined position.

According to one preferred embodiment of the invention, the splint support includes first and second complementary hook-and-loop elements on respective matable surfaces of the bandage and the splint.

According to another preferred embodiment of the invention, the splint support includes a vertically-extending pocket formed in the bandage for positioning and supporting the splint in a vertically-extending position against the knee.

According to yet another preferred embodiment of the invention, the substrate includes a plurality of knitted or woven fabric layers.

According to yet another preferred embodiment of the invention, the bandage includes a foam sheet material.

According to yet another preferred embodiment of the invention, the foam sheet material is selected from the group consisting of open or closed cell EVA or polyurethane.

According to yet another preferred embodiment of the invention, the bandage includes a fabric material covering at least one side of the foam sheet material.

According to yet another preferred embodiment of the invention, the flexible outer cover is formed of a material selected from the group consisting of woven, knitted or non-woven fabric.

According to yet another preferred embodiment of the invention, the reactive system includes a blended polyisocyanate, polyol, catalyst and stabilizer.

According to yet another preferred embodiment of the invention, the bandage is a tube for being pulled onto the leg over the foot.

According to yet another preferred embodiment of the invention, the bandage includes a flat sheet having cooperating mechanical fasteners for releasably holding the sheet around the knee.

According to yet another preferred embodiment of the invention, the mechanical fasteners include first and second complementary hook-and-loop elements on matable surfaces of said flat sheet.

According to yet another preferred embodiment of the invention, the knee immobilizer includes an elongate elastic strip for being wrapped around the knee over the bandage and splint during curing of the reactive system, thereby holding the bandage and splint in a closely conforming position on the knee.

According to yet another preferred embodiment of the invention, the splint is approximately one inch wide.

According to yet another preferred embodiment of the invention, the knee immobilizer includes at least one retaining strap for releasably encircling and maintaining the bandage and splint in supporting position on the knee.

According to yet another preferred embodiment of the invention, a knee immobilizer is provided for being custom-formed to the shape of a knee while flexible and upon hardening providing a rigid, knee-supporting custom fit. The knee immobilizer includes an elongate splint with a substrate. A reactive system is impregnated into or coated onto the substrate, the system remaining stable when maintained in substantially moisture-free conditions and hardening upon exposure to moisture to form a rigid, self supporting structure. An outer cover is positioned over and encloses the substrate. The substrate and outer cover form a unitary structure for being molded while flexible to an aspect of the knee. The knee immobilizer also includes a bandage for extending around the knee and holding said splint in a closely-conforming configuration around the knee and a splint support cooperating with the splint and the bandage for maintaining the splint on the bandage in the closely conforming position against the knee and substantially immobilizing the knee in a predetermined position.

According to yet another preferred embodiment of the invention, a knee immobilizer product is provided for being custom-formed to the shape of a knee while flexible and upon hardening providing a rigid, knee-supporting custom fit. The knee immobilizer product includes an outer pouch formed of moisture-impervious material and an elongate splint. The splint includesa substrate impregnated or coated with a reactive system. The system hardens upon exposure to moisture to form a rigid, self-supporting structure. A flexible protective cover overlies the substrate for forming an integrated splint structure for being molded while flexible to an aspect of the knee. The knee immobilizer product also includes a bandage for extending around the knee and holding the splint in a supporting position on the knee. A splint support cooperates with the splint and the bandage for maintaining the splint on the bandage in a conforming shape against the knee and substantially immobilizing the knee in a predetermined position.

An embodiment of the method of therapeutically immobilizing a knee is provided. The method includes the steps of providing a knee splint. The splint includes an elongate substrate. A reactive system is impregnated into or coated onto the substrate, the system remaining stable when maintained in substantially moisture-free conditions and hardening upon exposure to moisture to form a rigid, self supporting structure. A flexible outer cover is positioned over and encloses the substrate, the substrate and outer cover forming a unitary structure for being molded while flexible to an aspect of the knee. The method also includes the steps of providing a bandage for being positioned on and held in a closely-conforming configuration around the knee and providing a splint support cooperating with the splint and the bandage for maintaining the splint on the bandage in a closely conforming position against the knee and substantially immobilizing the knee in a predetermined position. The method further includes the steps of placing the bandage in a closely-conforming configuration around the knee, wetting the splint, placing the splint into engagement with the bandage by cooperation with the splint support against the knee and thereby substantially immobilizing the knee in a predetermined recovery position. The bandage and engaged splint are maintained in the closely-conforming configuration for a period of time sufficient to allow the reactive system to harden the splint.

According to another preferred embodiment of the invention, the step of placing the bandage in a closely-conforming configuration around the knee and adjacent thigh and calf portions of the leg comprises the step of pulling a tubular bandage over the foot and onto the knee portion of the leg.

According to yet another preferred embodiment of the invention, the step of placing the bandage in a closely-conforming configuration around the knee and adjacent thigh and calf portions of the leg comprises the step of placing a flat sheet around the knee and releasably securing the sheet around the knee with mechanical fasteners.

According to yet another preferred embodiment of the invention, the step of securing the sheet around the knee with mechanical fasteners includes the step of connecting first and second complementary hook-and-loop elements carried on matable surfaces of the flat sheet.

According to yet another preferred embodiment of the invention, the method includes the step of maintaining the bandage and engaged splints in the closely-conforming configuration for a period of time sufficient to allow the resin to harden the splints comprises the step of wrapping an elongate elastic strip around the knee over the bandage and splints during curing of the moisture-curable resin, thereby holding the bandage and splints in closely conforming position on the knee.

According to yet another preferred embodiment of the invention, the step of placing the splints into engagement with the bandage comprises the step of inserting the splints into respective vertically-oriented pockets formed in the bandage.

According to yet another preferred embodiment of the invention, the step of placing the splints into engagement with the bandage comprises the step of attaching to the bandage with complementary hook-and-loop elements.

BRIEF DESCRIPTION OF THE DRAWINGS

Some of the objects of the invention have been set forth above. Other objects and advantages of the invention will appear as the description proceeds when taken in conjunction with the following drawings, in which.

DESCRIPTION OF THE PREFERRED EMBODIMENT AND BEST MODE

Figure 1:
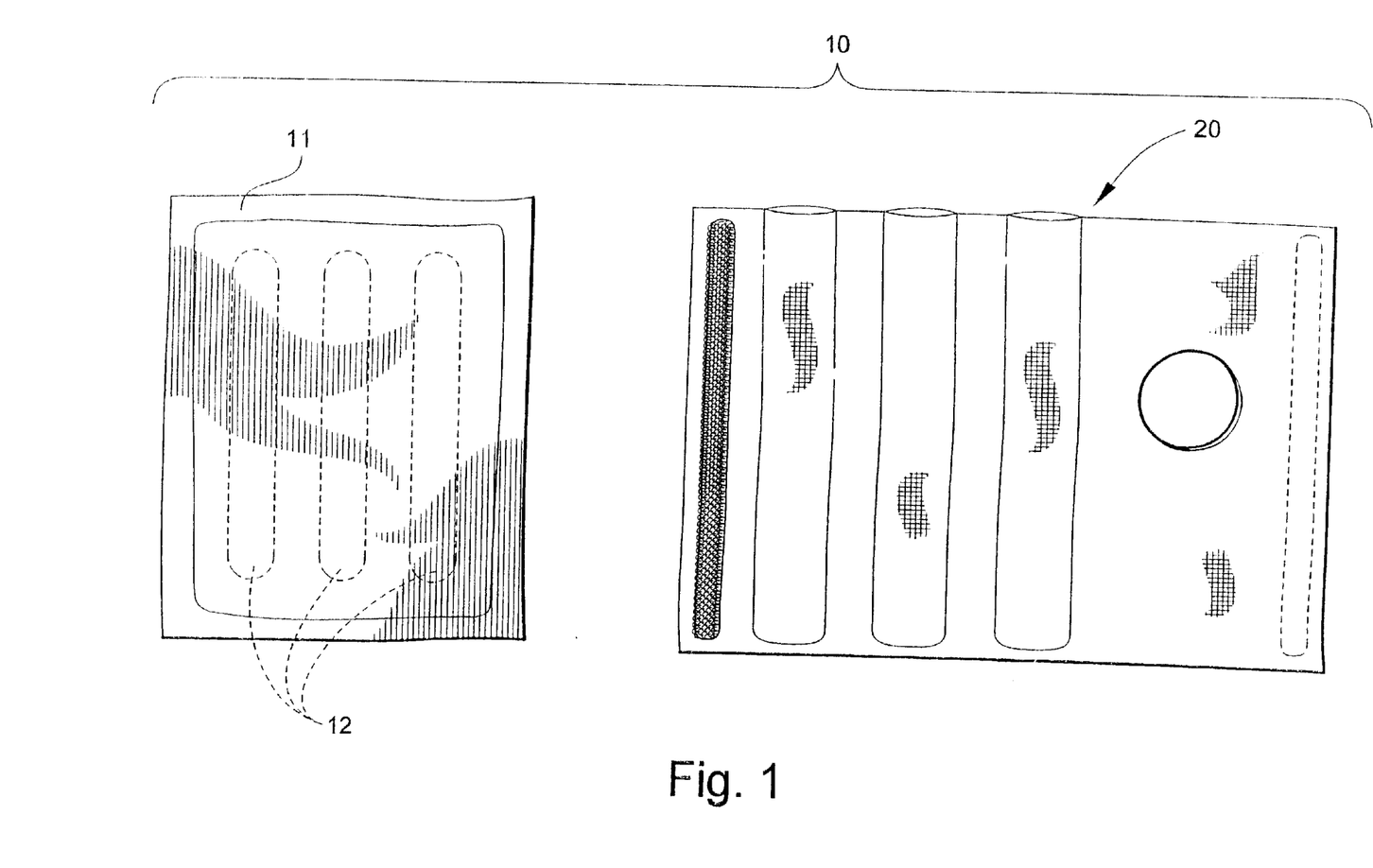
FIG. 1 illustrates a knee immobilizer product according to one preferred embodiment of the invention, which includes a protective pouch in which the immobilizer is stored until use.
Figure 2:
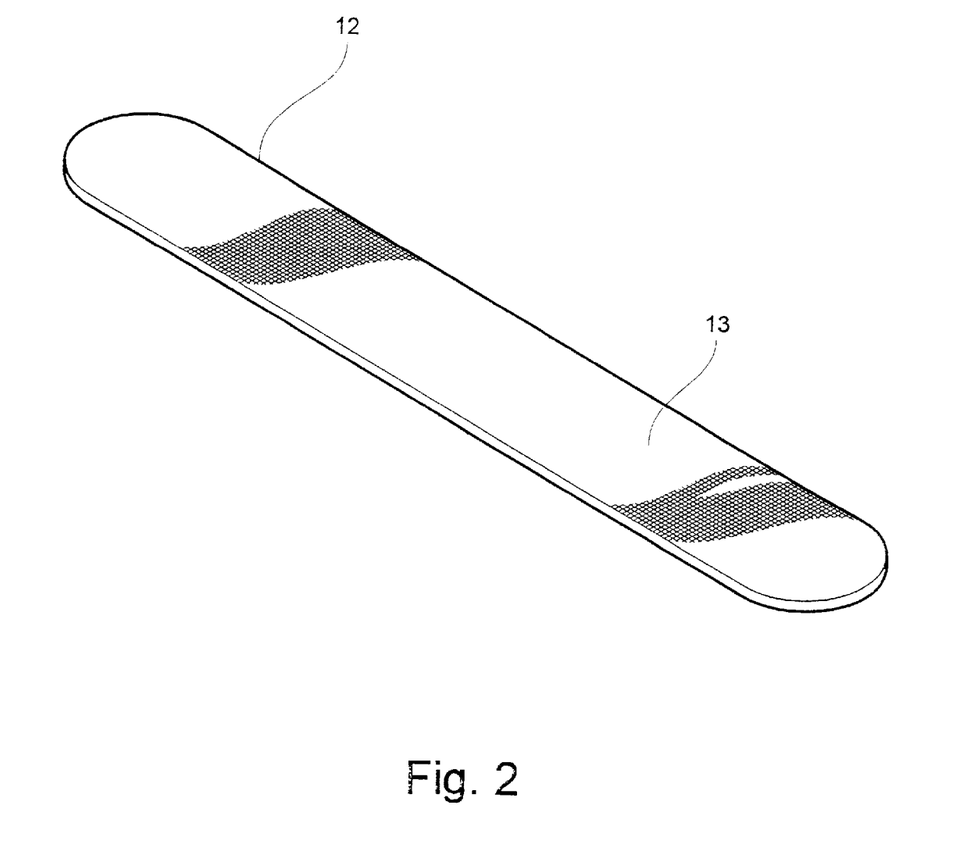
FIG. 2 is a perspective view showing a splint according to another embodiment of the invention.

Referring now specifically to the drawings, a knee immobilizer product according to a preferred embodiment of the invention is illustrated in FIG. 1 and shown broadly at reference numeral 10. A sealed, moisture-impervious foil and plastic laminated pouch 11 is fabricated of a aluminum foil laminate having an outer tear resistant layer, a central aluminum foil layer and an inner heat sealable plastic layer. Pouch 11 is opened with scissors or a knife, and several knee splints 12, such as the knee splint 12 shown in FIG. 2, are removed. Any number of splints 12, including a single such splint 12, can be packaged in a single pouch 11. As discussed in detail below, the product 10 also includes a bandage 20, which is adapted for receiving the splints 12.

Figure 3:
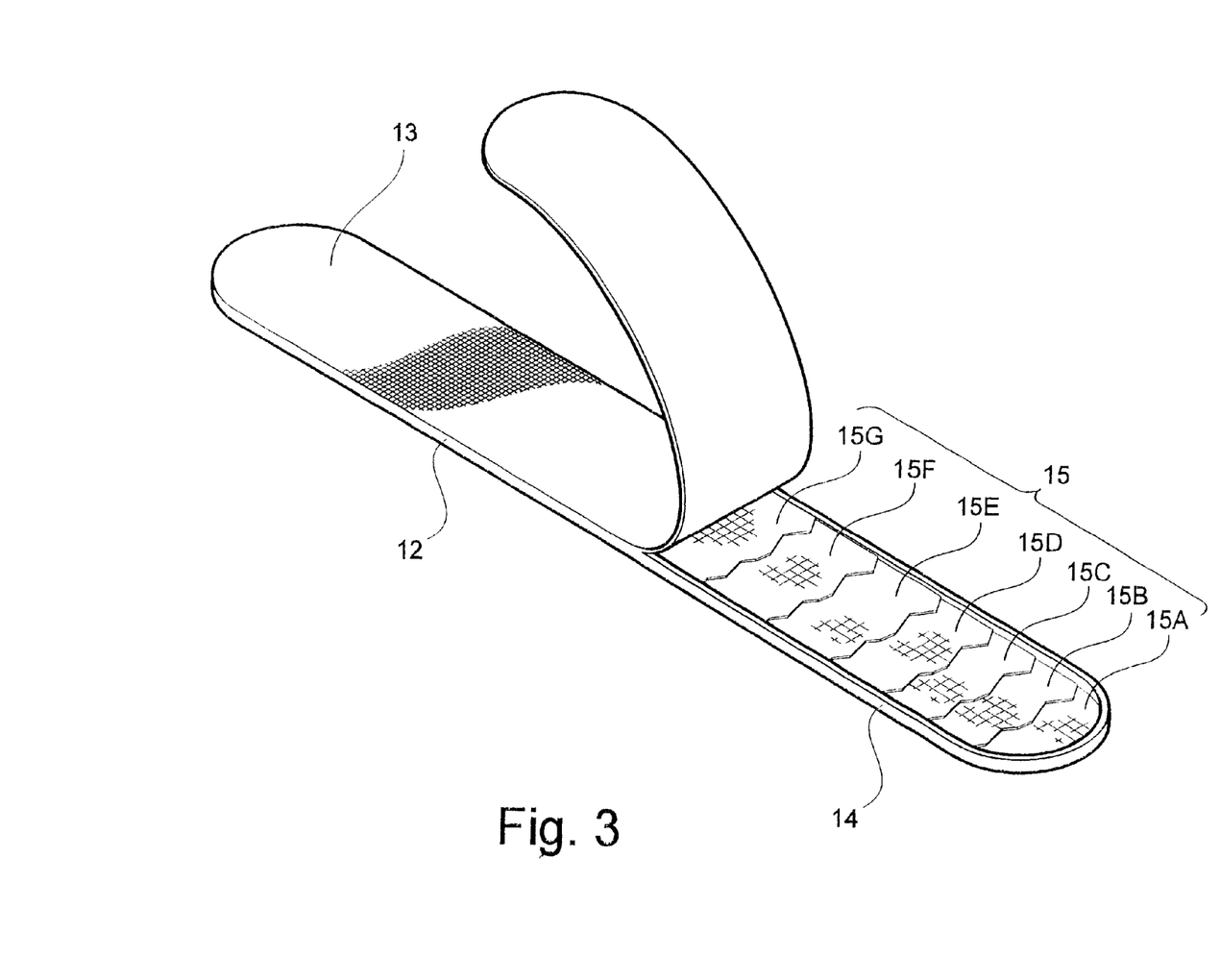
FIG. 3 is a fragmentary perspective view of the splint of FIG. 2, with parts of the substrate layers broken away for clarity.

As is shown in FIG. 3, splint 12 is formed from two outer covers 13, 14 of soft fibrous material, such as non-woven polypropylene. The outer covers 13 and 14 may be formed from a single sheet of material folded together form the two covers 13, 14, or may be formed from two individual sheets.

A substrate 15 is sandwiched between the two covers 13, 14, and is preferably formed from multiple fabric layers 15A–G, which are overlaid in registration with each other to form a laminated structure. The fabric layers 15A–G may be knitted, woven, or non-woven fiberglass fabric such as presently used in the ORTHOGLASS brand splinting material manufactured by applicant. Other fabric material and constructions, such as knitted polypropylene, can also be used to form the substrate 15.

The fabric layers 15A–G of the substrate 15 are impregnated or coated with a moisture-curable resin such as the polyisocyanate described in full in the present applicant's U.S. Pat. No. 4,770,299. This reactive system remains stable when maintained in substantially moisture-free conditions, such as in the moisture-impervious pouch 11, see FIG. 1, but hardens upon exposure to sufficient moisture to form a rigid, self-supporting structure. A typical formulation of the reactive system is set forth in the following table:

| Typical Formulation: | | |
|---|---|---|
| Isonate ↓ 143L or Mondur ↓ CD or Rubinate ↓ XI168 | polyisocyanate | 50.0% |
| Pluracol ↓ P1010 | polyol | 46.6% |
| DC-200 Silicone | defoaming agent | 0.30% |
| Benzoyl Chloride | stabilizer | 0.10% |
| Thancat ↓ DM-70 | catalyst | 3.0% |
| | | 100% |

A complete discussion of the parameters of the reactive system, the manner of production and the variables which apply are found in U.S. Pat. No. 4,411,262.

Figure 4:
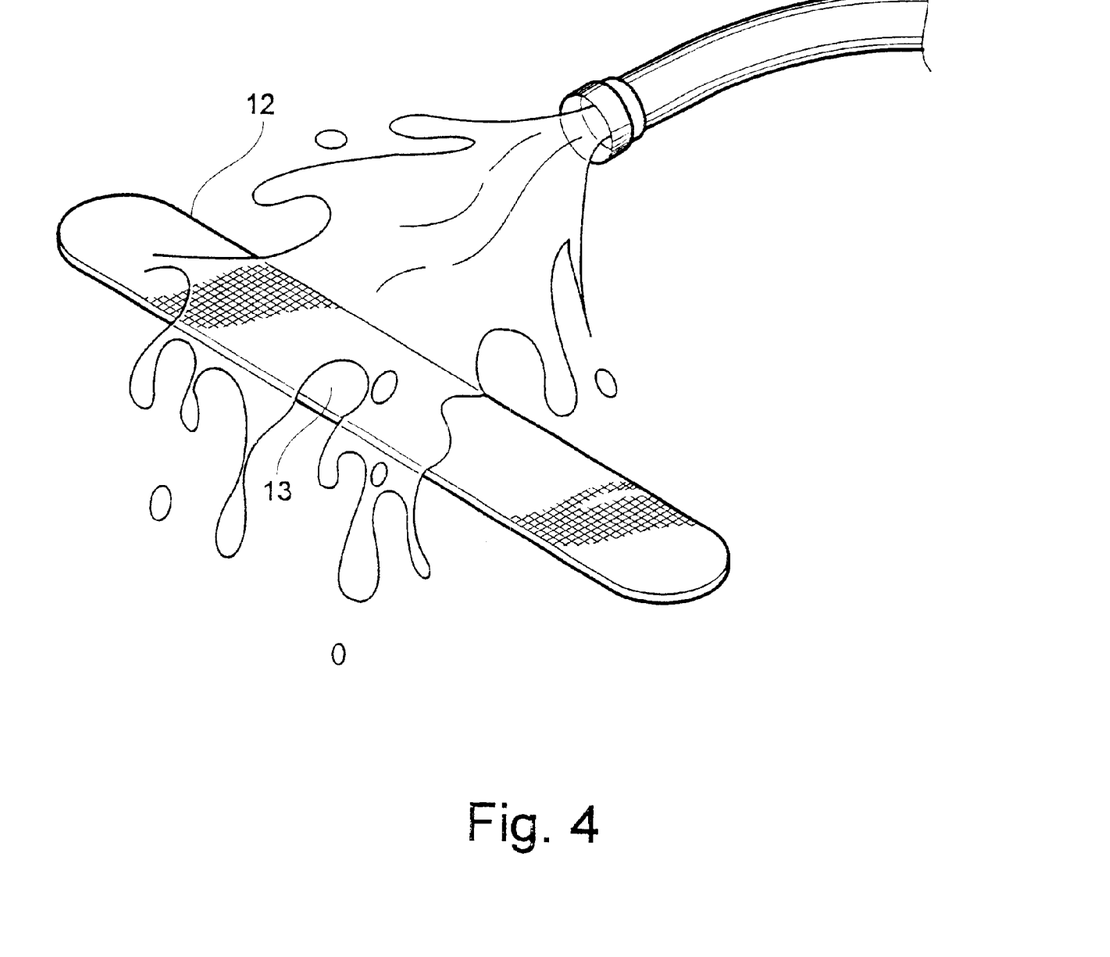
FIG. 4 illustrates a splint being wetted with water, for example by spraying, before the splint is custom-fitted to a knee.

The polyisocyanate resin remains in a viscous, liquid unhardened state so long as the resin is not exposed to moisture. This permits the fiberglass layers 15A–G to remain flexible and moldable until as the resin is exposed to moisture, and for a relatively short period of time afterward. The curing time can be controlled to some extent by the quantity of water to which the resin is exposed. For example, exposure to water by dipping will result in quite rapid curing, while merely allowing the resin to be exposed to air will cause long curing times proportional to the amount of moisture in the air to which the resin is exposed. Spraying with a mist of water "W" from a spray bottle is also a preferred way of initiating the curing process. See FIG. 4.

The splint 12 is preferably a suitable length of splint material such as the material made and sold by applicant under the trademark ORTHOGLASS, and may be, for example, from one to two inches wide and from 12 to 24 inches long. The splint 12 may be supplied in an elongate roll form and cut to the exact length needed.

The resin coated or impregnated fiberglass layers 15A–G may alternatively be covered on one or both sides with a foam protective pad (not shown). Such a pad may be a single thickness or a laminated structure. This pad structure would substitute for the outer covers 13, 14. One preferred embodiment of a foam protective pad is a 3/16 inch, six pound EVA (ethylene vinyl acetate) pad. Another embodiment may be a 3/8 inch laminated pad of a 1/8 inch outer EVA pad and a 1/4 inch outer polyethylene/polyurethane, combination open and closed cell foam.

Figure 5:
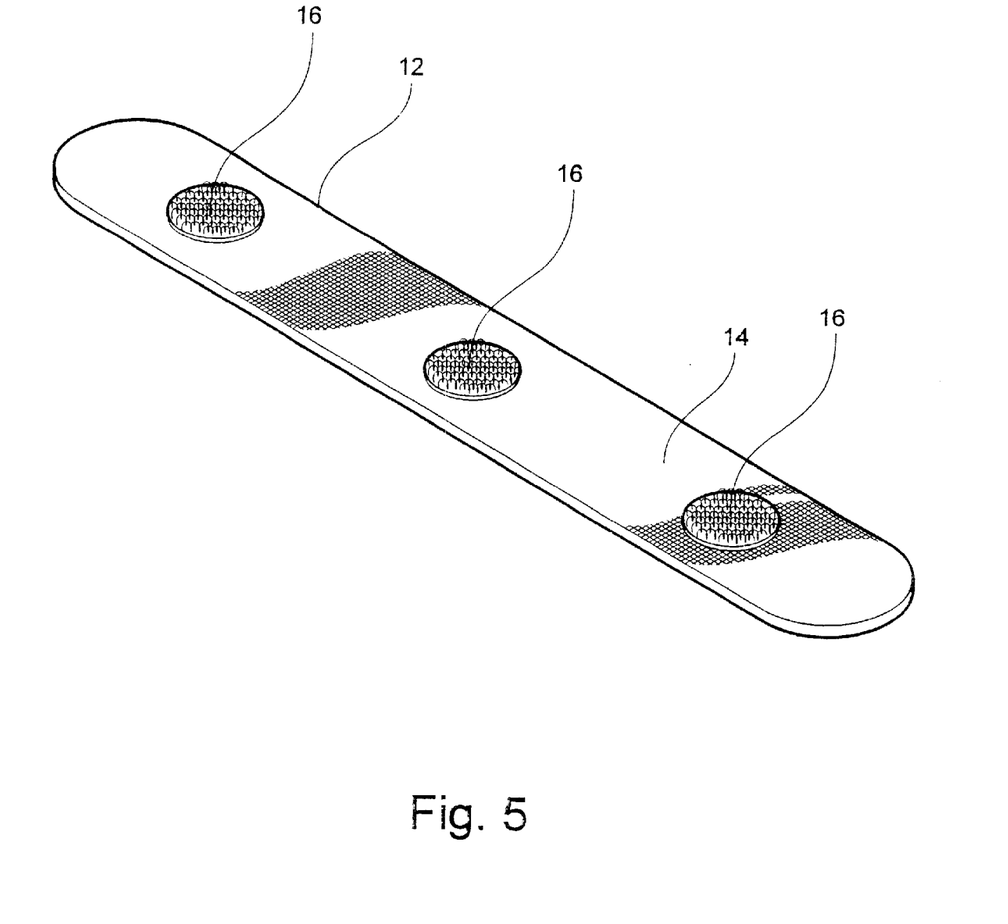
FIG. 5 is a perspective view of the reverse side of the splint shown in FIG. 2.

Referring now to FIG. 5, the reverse side of the knee splint 12 is shown, and includes a plurality of splint support elements in the form of patches 16 of hook (shown) or loop fastener (not shown) material positioned in spaced-apart relation along the length of the splint 12. Although any number of patches 16 may be used, three patches 16 are preferred.

Figure 6:
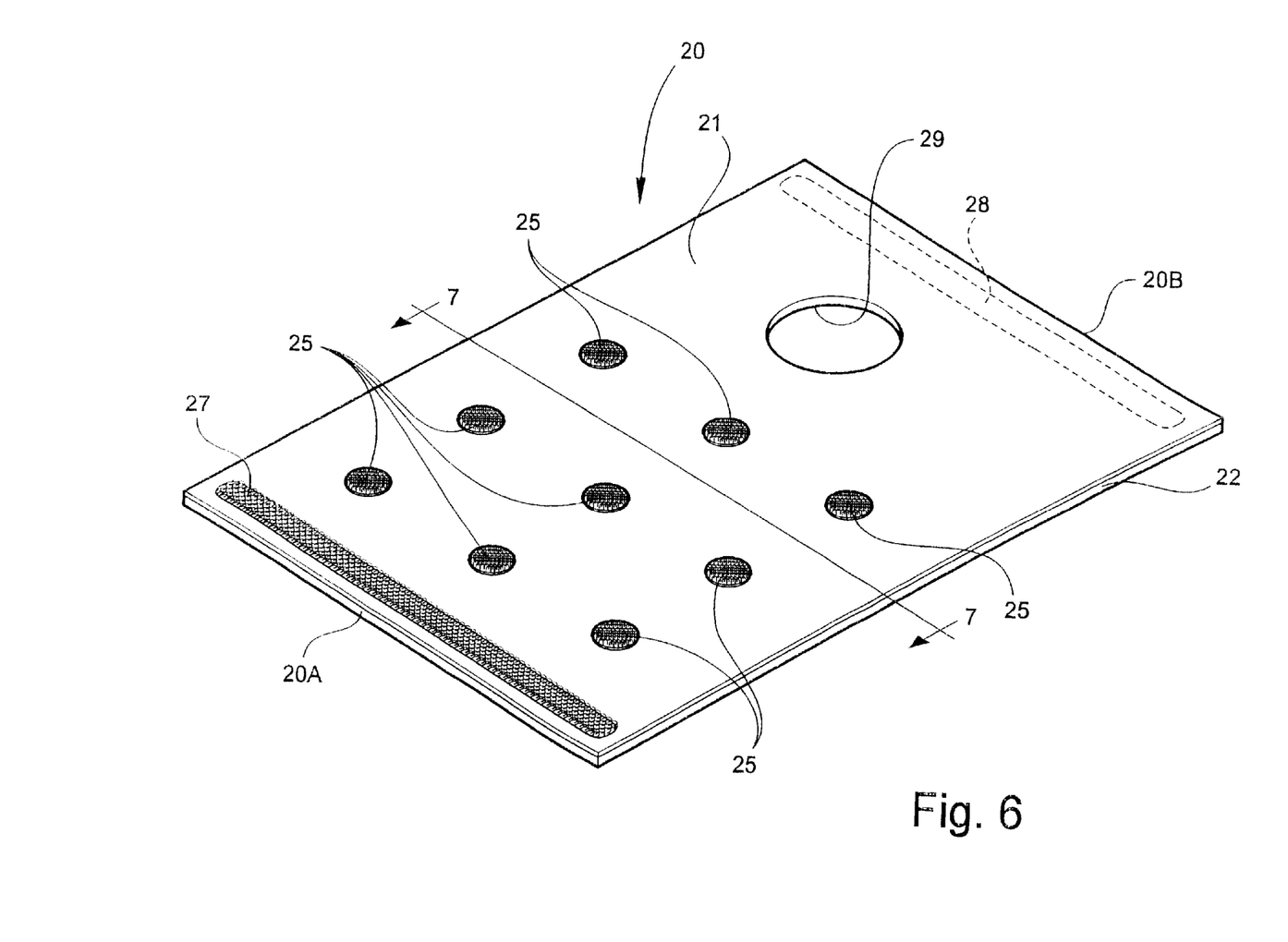
FIG. 6 is a perspective view of a bandage part of the knee immobilizer product according to one embodiment of the invention.
Figure 7:
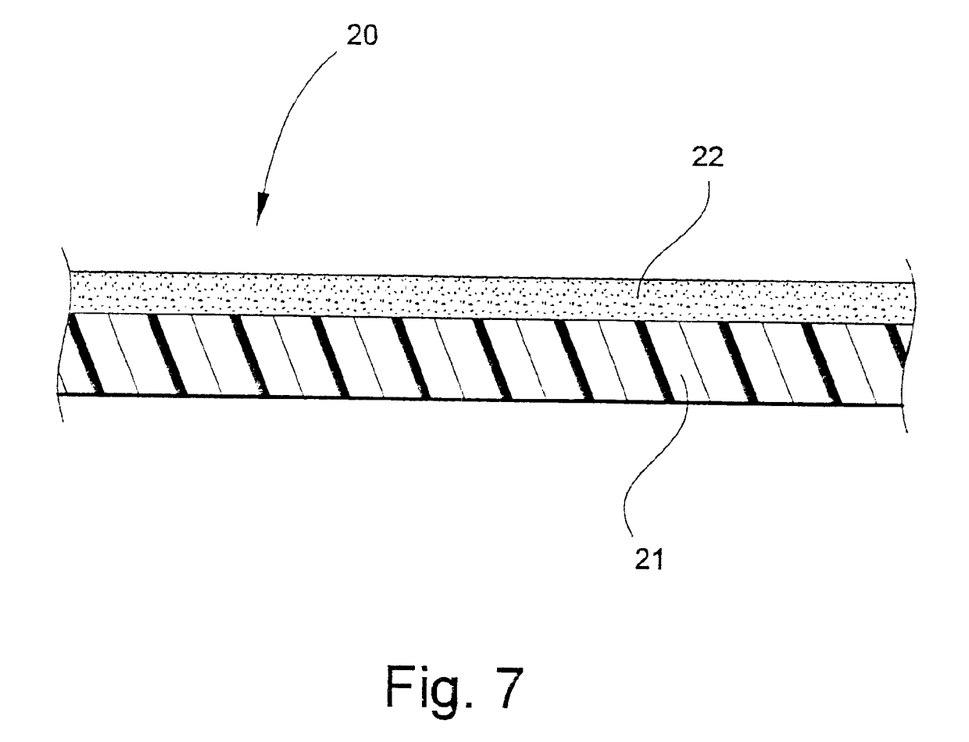
FIG. 7 is a cross-sectional view of the bandage part taken along line 7—7 of FIG. 6.

As is shown in FIG. 6, a bandage 20 according to one particular embodiment of the invention is shown. The bandage 20 is formed of a flat sheet 21 of open or closed cell EVA foam with a cover layer 22, which is preferably formed of a non-woven, synthetic cushion fabric such as a polypropylene fabric of the type used as the outer cover of the splint 12. The cover layer 22 may be used only on the inner side of the bandage 20, as shown in FIGS. 6 and 7, or may be used to cover both sides of the bandage 20 (not shown). The bandage 20 is preferably slightly tapered toward the bottom side edges 20A and 20B to as to properly fit the generally frusto-conical shape of the lower thigh, knee and upper calf. The bandage 20 shown in FIG. 6 also includes splint supports 25 positioned in three vertical rows on the outwardly-facing surface of the sheet 21. These splint supports 25 comprise patches of loops (shown) or hooks (not shown) which cooperate with the hooks 16 on each of the three splints 12 to secure the splints 12 in a vertical orientation along the outside of the bandage 20.

The bandage 25 is preferably held around the knee by adjustably connecting together a strip 27 of loops and a strip 28 of hooks, each of which is attached to a respective one of the opposite faces of opposite ends of the bandage 20. The bandage 20 may alternatively be provided with an outer cover of non-woven, looped fabric upon which the strip 28 of hooks can be adjustably engaged, thus making a separate patch of loops unnecessary.

An optional patella opening 29 is defined by and extends through the bandage 20 from one side to the other for exposing the patella to open air.

Figure 8:
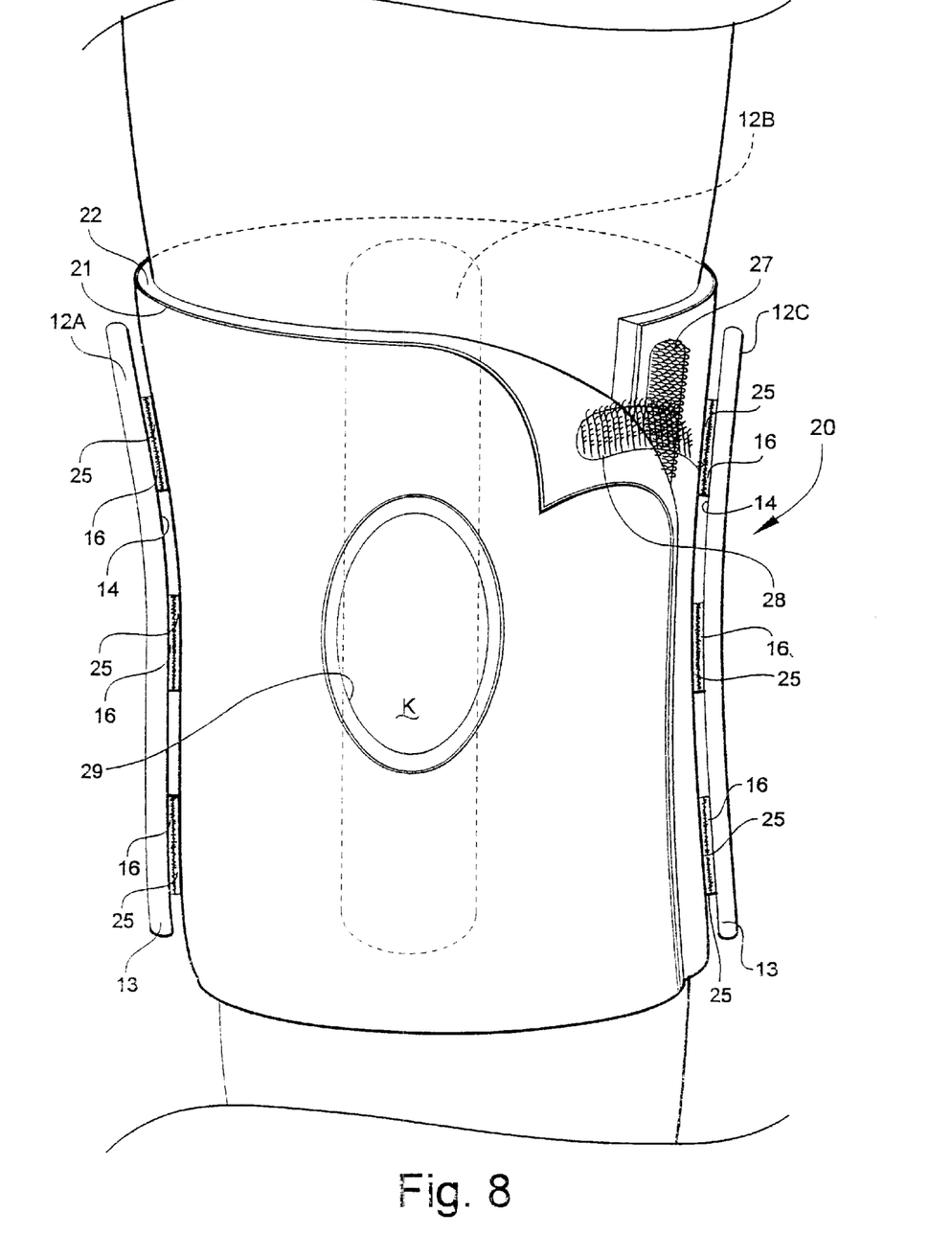
FIG. 8 is an environmental perspective view of the knee immobilizer shown correctly positioned on the knee, with an edge pulled away to show the attachment means.

Referring now to FIG. 8, the bandage 20 is shown in position on a knee "K". Note that three splints 12A, 12B and 12C extend along the respective lateral, posterior and medial aspects of the knee, thereby preventing articulation, eversion and inversion of the knee.

Figure 9:
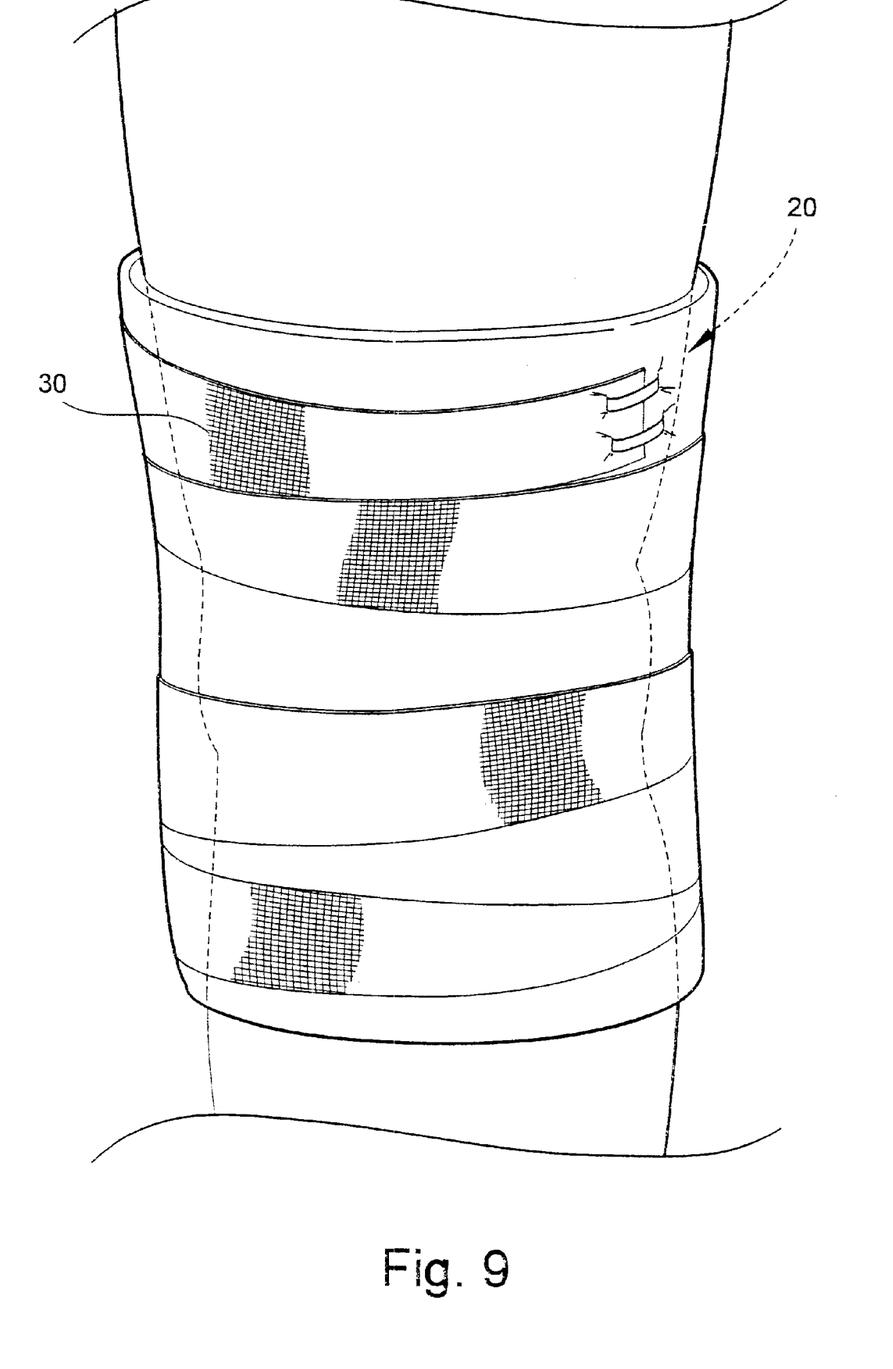
FIG. 9 is an environmental perspective view illustrating a preferred way in which the knee immobilizer is wrapped to hold the immobilizer in place during curing and during early stages of rehabilitation.
Figure 10:
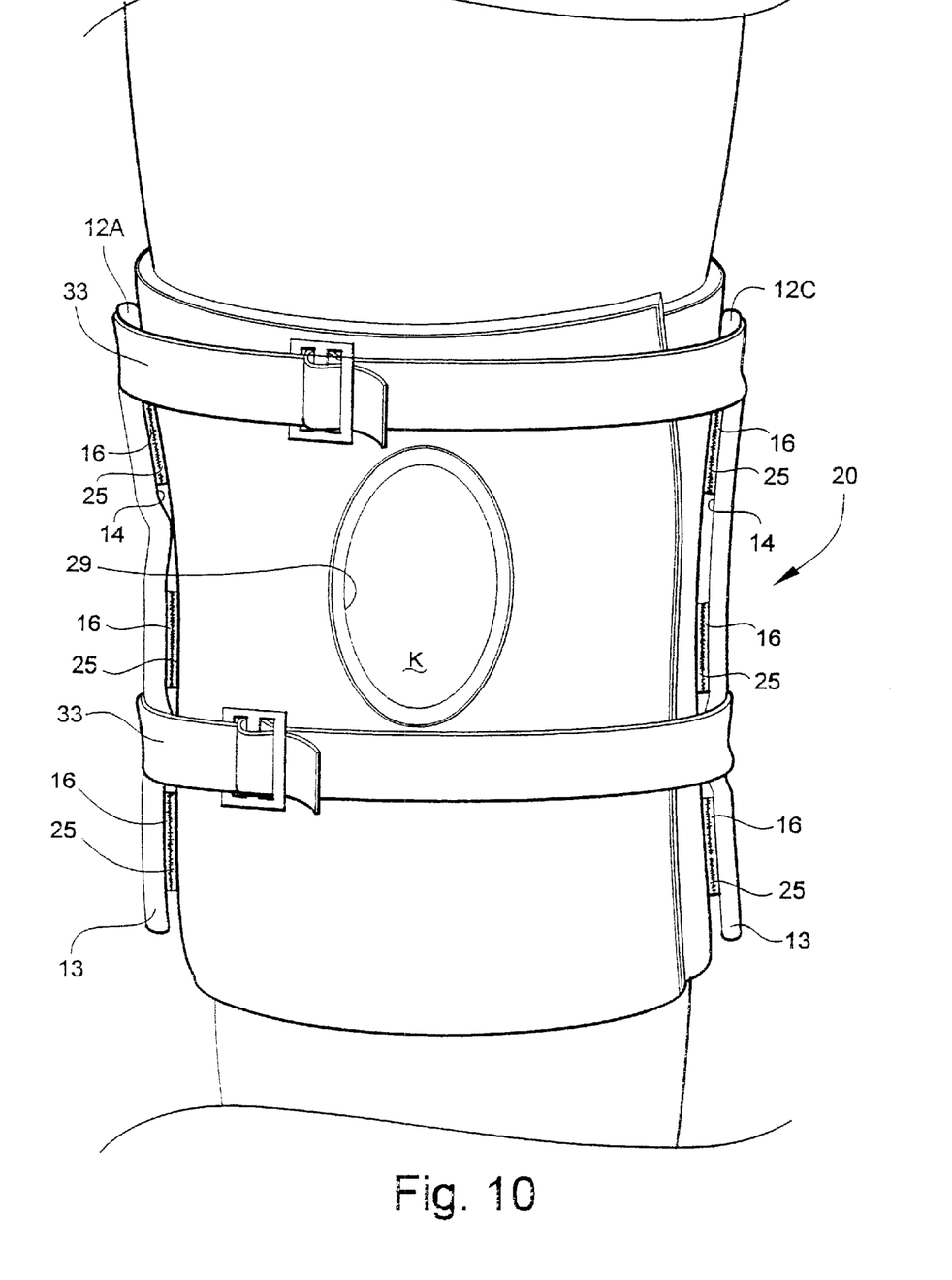
FIG. 10 is an environmental perspective view illustrating the knee immobilizer being held in place with straps, during, for example, the latter stages of rehabilitation.

As is shown in FIG. 9, the bandage 20 may be held in place during curing by a wrapping, such as a conventional strip of elastic medical bandage 30. The bandage 30 may also be worn during subsequent treatment as a way of maintaining the close fit of the knee immobilizer strips 12 around the knee and leg. Use of the conventional medical bandage 30 has been found to reduce edema during the early stages of recovery. An elastic fabric sock (not shown), may also be used to hold the bandage 20 in place during the curing process and/or during subsequent treatment. The sock is pulled over the foot, onto the leg and into position over the bandage 20. During later stages of recovery the bandage 20 may be held in place by conventional D-ring straps 33, as shown in FIG. 10.

Figure 11:
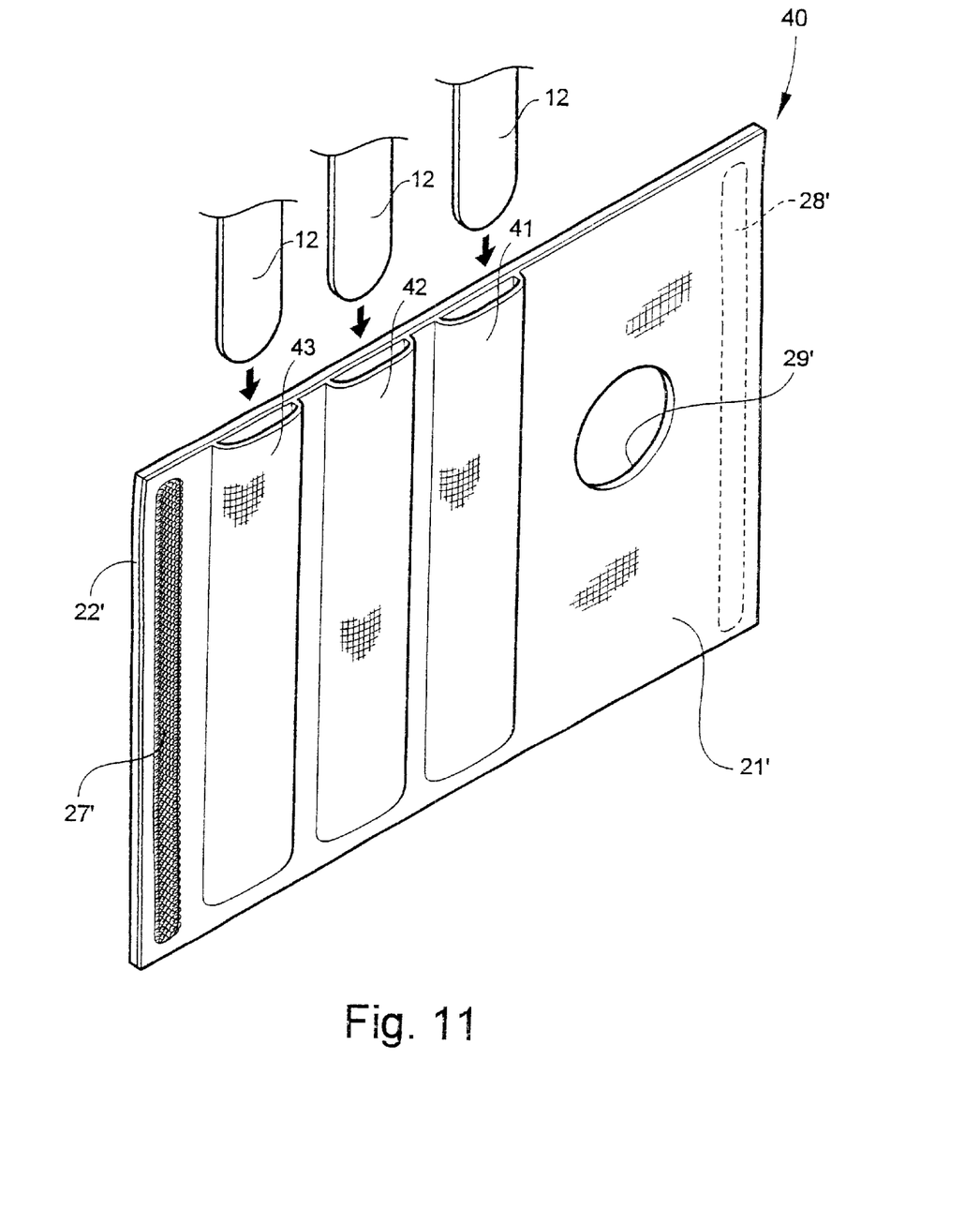
FIG. 11 is a perspective view of an alternative embodiment of the knee immobilizer with sewn pockets.
Figure 12:
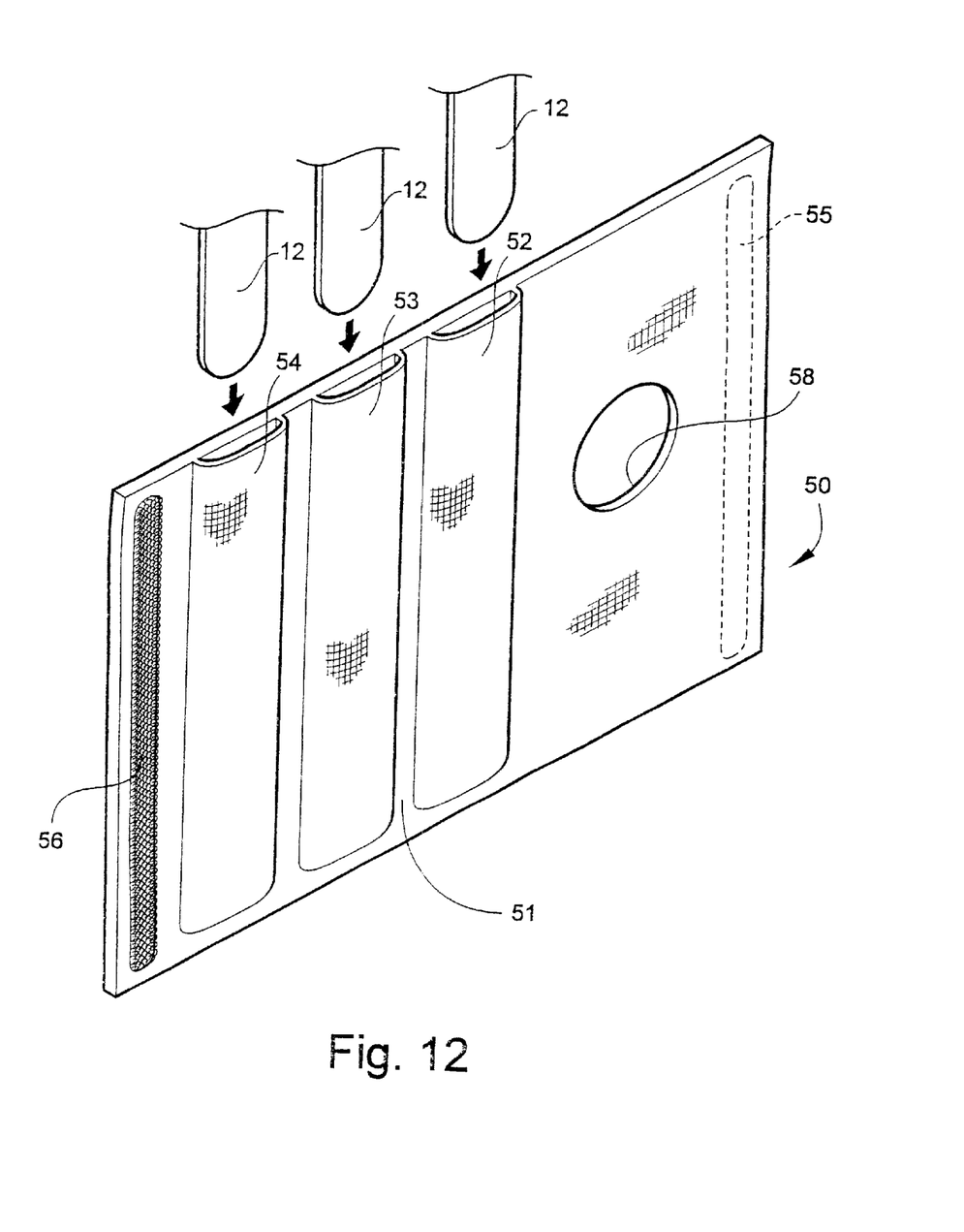
FIG. 12 is a perspective view of a further alternative embodiment of the invention showing the immobilizer with integrally-formed pockets.

Referring now to FIG. 11, an alternative embodiment of the bandage is shown generally at reference numeral 40. The bandage 40 is constructed of materials as described above, and is provided with three vertically-oriented splint supports in the form of pockets 41, 42, 43 positioned on the outer surface of the bandage 40. Components and elements of bandage 40 like those of in the bandage 20 are indicated using prime notation. The pockets 41, 42 and 43 may be formed by sewing, ultrasonically welding, gluing or otherwise adhering strips of fabric to the outer surface of the bandage 40. As is shown in FIG. 12, a bandage 50 can alternatively be fabricated by adhering a fabric 51 to the outer surface of the bandage 50, leaving unadhered, vertically-oriented strips that create splint supports in the form of pockets 51, 52, 53 for receiving the splints 12. As described above, hook and loop strips 55 and 56 permit the bandage 50 to be positioned and held around the knee. A patella opening 58 is optionally provided.

Three splints 12' are positioned in a respective one of the pockets 52, 53 and 54 either before or after the splints 12' are wetted. The bandage 40 is then wrapped around the knee and is maintained in position during curing, as well as during initial stages of recovery, if desired. See FIG. 11. During later stages of recovery, the bandage 50 may be held in place by conventional D-ring straps, as shown in FIG. 10.

Figure 13:
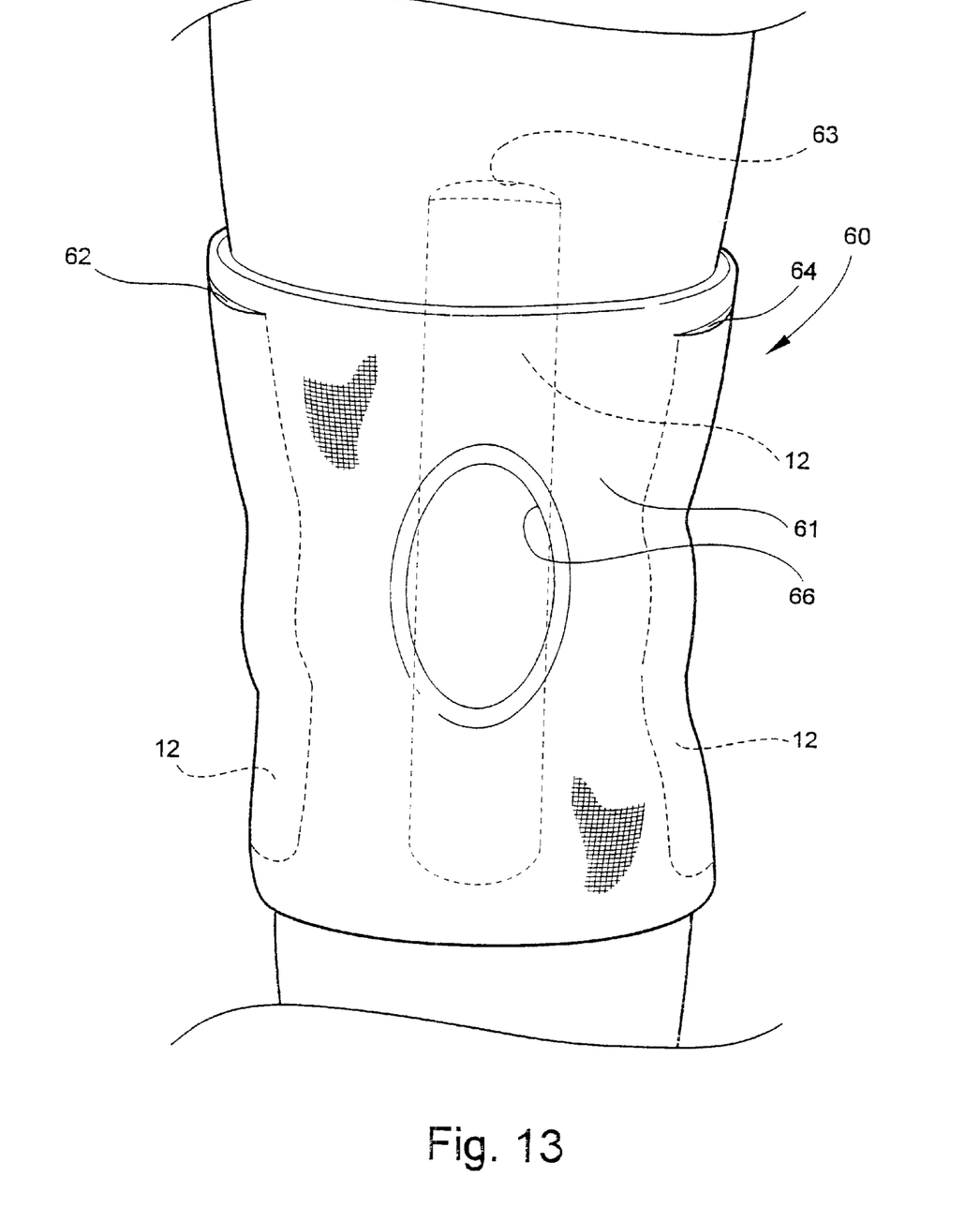
FIG. 13 is an environmental perspective view of a tubular embodiment of the invention in place on a knee.

Referring now to FIG. 13, an additional embodiment of the bandage according to the invention is shown in place on a knee and is shown generally at reference numeral 60. The bandage 60 is formed of a tube 61 of a conventional elastic knitted or woven medical fabric and is provided with splint supports in the form of three pockets 62, 63 and 64 which extend vertically along respective lateral, medial and posterior aspects of the knee. A patella opening 66 is optionally provided. A splint 12 according to the above disclosure is positioned in each of the pockets 62, 63, and 64, either before or after the splint has been wetted. The elastic structure of the tube 61 conforms the splints 62, 63 and 64 to the knee, lower thigh and upper calf, respectively. If additional conformation is desired, the bandage 60 can be wrapped with a strip an elastic medical bandage material, as described above and shown in FIG. 9.

Wetting of the splints 12 can be either before or after placement of the splints in the various embodiments of the bandages.

A knee immobilizer and method of immobilizing a knee is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim:

1. A method of therapeutically immobilizing a knee, comprising the steps of:
    (a) providing a knee splint, comprising:
        (i) an elongate substrate;
        (ii) a reactive system impregnated into or coated onto said substrate, the system remaining stable when maintained in substantially moisture-free conditions and hardening upon exposure to moisture to form a rigid, self supporting structure; and
        (iii) a flexible outer cover positioned over and enclosing the substrate, the substrate and outer cover forming a unitary structure for being molded while flexible to an aspect of the knee;
    (b) providing a bandage for being positioned on and held in a closely-conforming configuration around the knee; and
    (c) providing a splint support cooperating with said splint and said bandage for maintaining the splint on the bandage in a closely conforming position against the knee and substantially immobilizing the knee in a predetermined position;
    (d) placing the bandage in a closely-conforming configuration around the knee;
    (e) wetting the splint;
    (f) placing the splint into engagement with the bandage by cooperation with said splint support against the knee and thereby substantially immobilizing the knee in a predetermined recovery position; and
    (g) maintaining the bandage and engaged splint in the closely-conforming configuration for a period of time sufficient to allow the reactive system to harden the splint.

2. A method according to claim 1, wherein the step of placing the bandage in a closely-conforming configuration around the knee comprises the step of pulling a tubular bandage over the foot and onto the knee portion of the leg.

3. A method according to claim 1, wherein the step of placing the bandage in a closely-conforming configuration around the knee comprises the stop of placing a flat sheet around the knee and releasably securing the sheet around the knee with mechanical fasteners.

4. A method according to claim 1, including the step of maintaining the bandage and engaged splints in the closely-conforming configuration for a period of time sufficient to allow the resin to harden the splints comprises the step of wrapping an elongate elastic strip around the knee over the bandage and splints during curing of the moisture-curable resin and thereby holding the bandage and splints in closely conforming position on the knee.

5. A method according to claim 1, wherein the step of placing the splints into engagement with said bandage comprises the step or inserting the splints into respective vertically-oriented pockets formed in said bandage.

\* \* \* \* \*

UNITED STATES PATENT AND TRADEMARK OFFICE
CERTIFICATE OF CORRECTION

PATENT NO. : 6,712,780 B2
APPLICATION NO. : 10/271961
DATED : March 30, 2004
INVENTOR(S) : Thomas D. Darcey It is certified that error appears in the above-identified patent and that said Letters Patent is hereby corrected as shown below:

Column 9, line 7, delete "stop" and enter --step--.

Column 9, line 10, delete "claim 1, including" and enter --claim 1, and including--.

Column 10, line 8, delete "or" and enter --of--.

Signed and Sealed this

Nineteenth Day of December, 2006

JON W. DUDAS
*Director of the United States Patent and Trademark Office*